(12) United States Patent
Kang et al.

(10) Patent No.: US 9,012,178 B2
(45) Date of Patent: Apr. 21, 2015

(54) DIPEPTIDES TO ENHANCE YIELD AND VIABILITY FROM CELL CULTURES

(75) Inventors: Sohye Kang, Torrance, CA (US); Rohini Deshpande, Camarillo, CA (US); Rebecca E. McCoy, Port Orchard, WA (US); Leslie P. Miranda, Thousand Oaks, CA (US); Arvia E. Morris, Seattle, WA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 13/814,397

(22) PCT Filed: Aug. 5, 2011

(86) PCT No.: PCT/US2011/046850
§ 371 (c)(1),
(2), (4) Date: Apr. 8, 2013

(87) PCT Pub. No.: WO2012/019160
PCT Pub. Date: Feb. 9, 2012

(65) Prior Publication Data
US 2013/0189737 A1    Jul. 25, 2013

Related U.S. Application Data

(60) Provisional application No. 61/371,119, filed on Aug. 5, 2010.

(51) Int. Cl.
| | | |
|---|---|---|
| *C12P 21/04* | (2006.01) | |
| *C07K 16/00* | (2006.01) | |
| *C07K 5/062* | (2006.01) | |
| *C07K 5/065* | (2006.01) | |
| *C07K 5/072* | (2006.01) | |
| *C12N 5/00* | (2006.01) | |

(52) U.S. Cl.
CPC ............... *C07K 16/00* (2013.01); *C07K 5/0606* (2013.01); *C07K 5/06078* (2013.01); *C07K 5/06104* (2013.01); *C07K 2317/14* (2013.01); *C12N 5/0037* (2013.01); *C12N 2500/32* (2013.01); *C12N 2500/46* (2013.01); *C12N 2501/105* (2013.01); *C12N 2501/998* (2013.01); *C12N 2510/02* (2013.01)

(58) Field of Classification Search
None
See application file for complete search history.

(56) References Cited

U.S. PATENT DOCUMENTS

| | | | |
|---|---|---|---|
| 5,534,538 A | 7/1996 | Drauz | |
| 2008/0254513 A1* | 10/2008 | Cayli | ........................... 435/70.1 |
| 2011/0262965 A1 | 10/2011 | Barrett | |

FOREIGN PATENT DOCUMENTS

| | | |
|---|---|---|
| WO | WO 97/30713 A1 | 8/1997 |
| WO | WO 2008/154014 A2 | 12/2008 |
| WO | WO 2010/050448 A1 | 5/2010 |

OTHER PUBLICATIONS

CD FortiCHO documention Retrieved from < http://www.lifetechnologies.com/order/catalog/product/A1148301 > on May 29, 2014.*
Yasufumi Imamoto et al., "Advantage of AlaGln as and Additive to Cell Culture Medium", Animal Cell Technology: Basic & Applied Aspects, 2010, pp. 65-71.
Keen et al., "Developement of a Serum-Free Culture Medium for the Large Scale Production of Recombinant Protein from a Chinese Hamster Ovary Cell Line", Cytotechnology, 1995, 17: pp. 153-163.
Purdie et al., "Algorithms for the Quantitative Validation of Chiral Properties of Peptides", Chirality, 1999, 11 (7) : pp. 546-553.
Simpkins, "A New Cytochrome C Reducing Dipeptide", J Nat Med Assoc USA, 1990, 82 (2) : pp. 113-116.
Stryer L, (1989) "Biochemistry" 2nd edn., (pub. WH Freeman, San Francisco, CA, USA); at p. 17.
Extract from PubChem (NCBI) website for L-alanine, L-tyrosyl (Tyr-Ala); Aug. 20, 2013.
Extract from PubChem (NCBI) website for L-tyrosine, L-alanyl (Ala-Tyr); Aug. 20, 2013.
Extract from SW3C website for L-alanine, L-tyrosyl (Tyr-Ala); Aug. 13, 2013.
Extract from SW3C website for L-tyrosine, L-alanyl (Ala-Tyr); Aug. 13, 2013.
Grillberger et al., "Emerging Trends in Plasma-Free Manufacturing of Recombinant Protein Therapeutics Expressed in Mammalian Cells", Biotechnology Journal, 2009, 4(2): pp. 186-201.
Franek et al., "Plant Protein Hydrolysates: Preparation of Defined Peptide Fractions Promoting Growth and Production in Animal Cells Cultures", Biogechnol. Prog., 2000, 16: pp. 688-692.
Franek et al., "Specific Effects of Synthetic Oligopeptides on Cultured Animal Cells", Biogechnol. Prog., 2002, 18: pp. 155-158.
Franek et al., "Survival Factor-Like Activity of Small Peptides in Hybridoma and CHO Cells Cultures", Biogechnol. Prog., 2005, 21: pp. 96-98.

* cited by examiner

*Primary Examiner* — Suzanne M Noakes
(74) *Attorney, Agent, or Firm* — Kathleen Fowler

(57) ABSTRACT

The present invention relates to the culture of animal cells in serum-free culture medium. The present invention provides particular dipeptides that can improve recombinant protein production and cell viability in such cultures, especially in the absence of peptones.

24 Claims, 10 Drawing Sheets

Figure 1- Effect of various di-peptides on titer and viability in Cell line A
Figure 1A- Titer
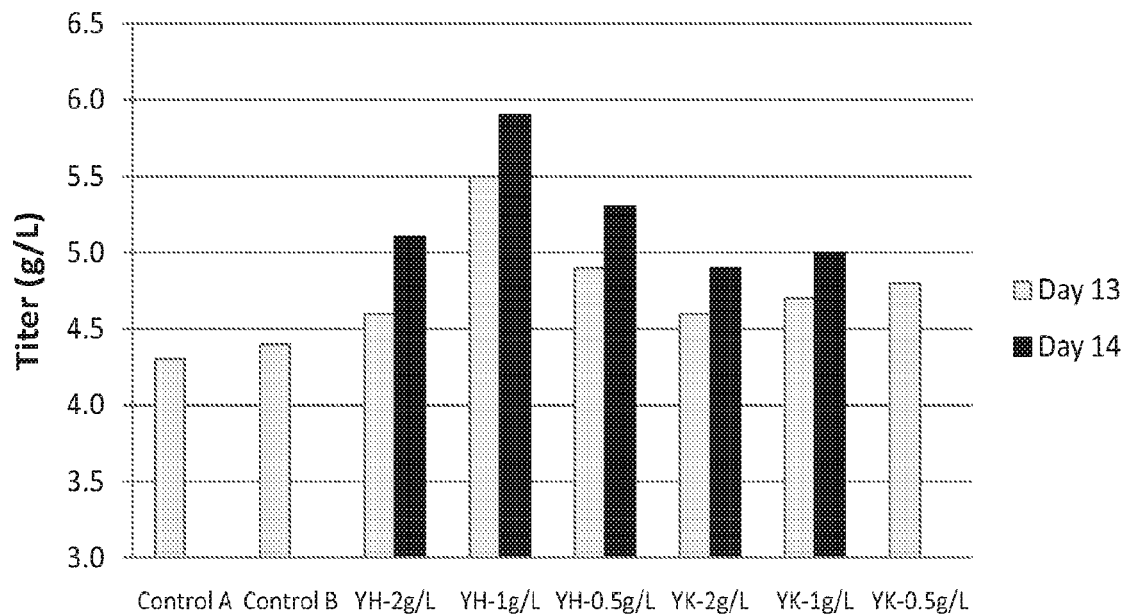
Figure 1B- Viability
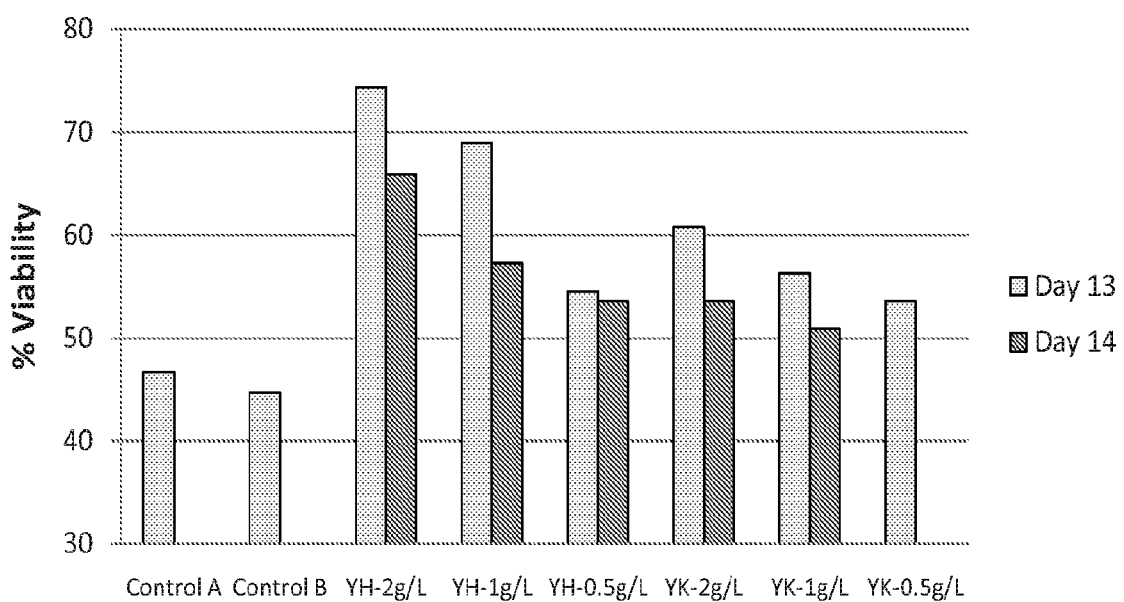

Figure 2- Effect of various di-peptides on titer and viability in Cell line B
Figure 2A- Titer
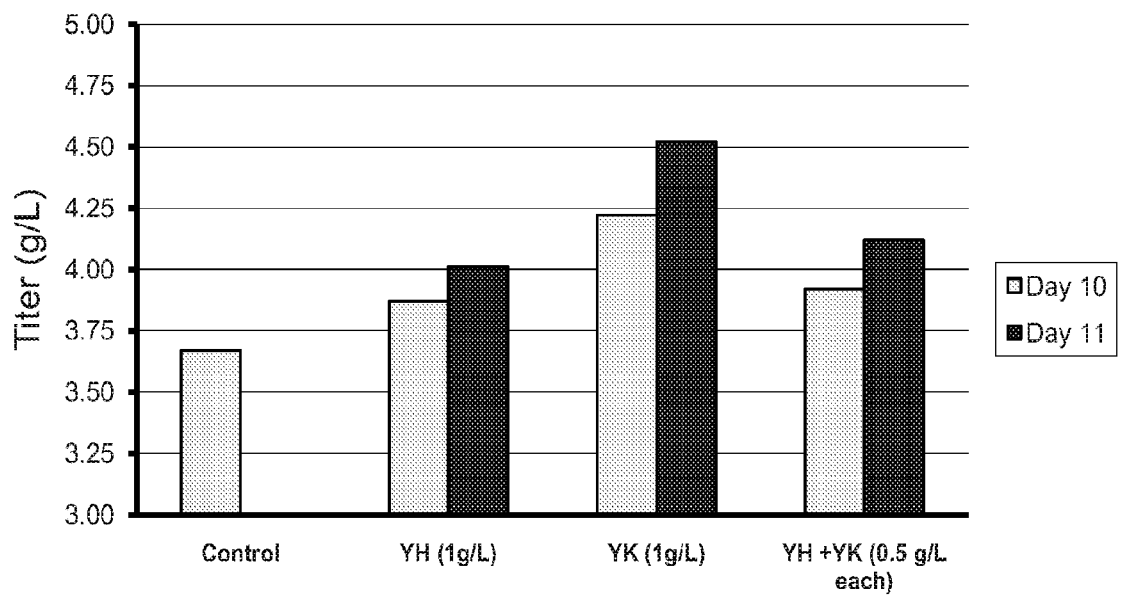
Figure 2B- Viability
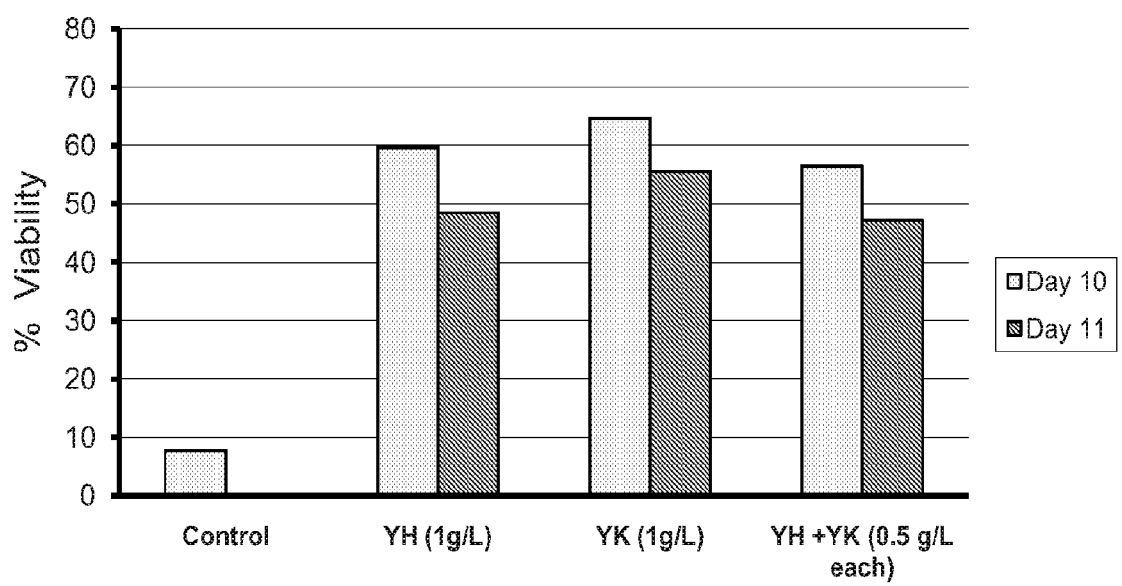

Figure 3- Effect of various di-peptides on titer and viability in Cell line C
Figure 3A- Titer
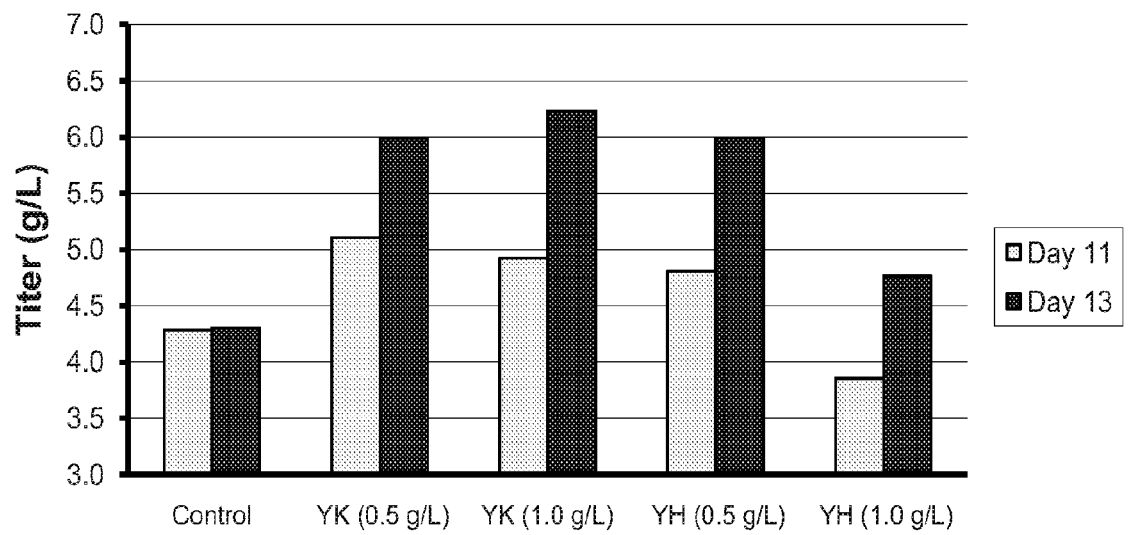
Figure 3B- Viability
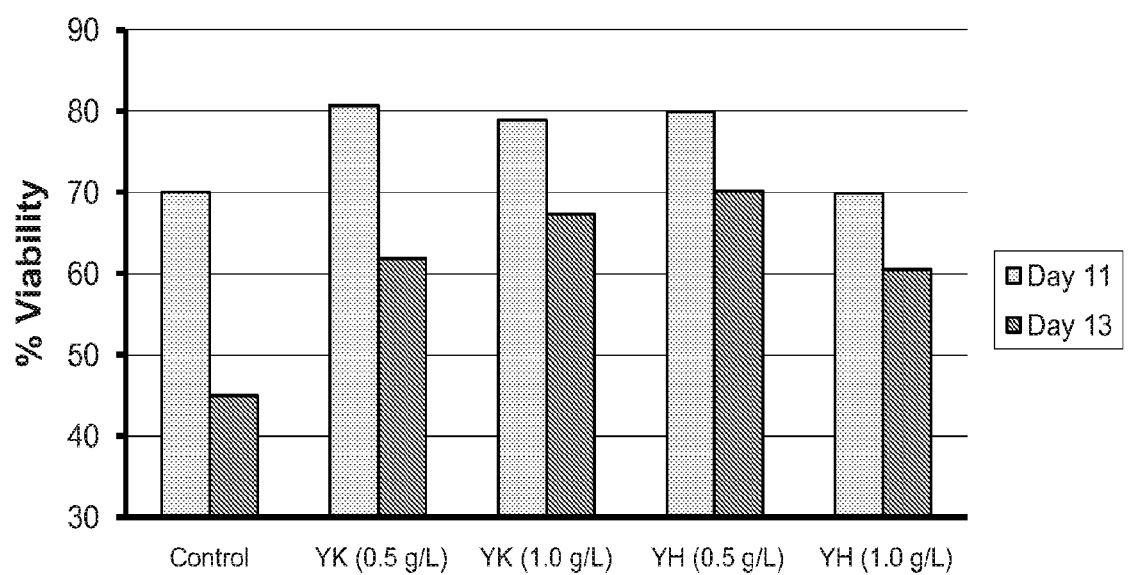

Figure 4- Effect of various di-peptides on titer and viability in Cell line D
Figure 4A- Titer
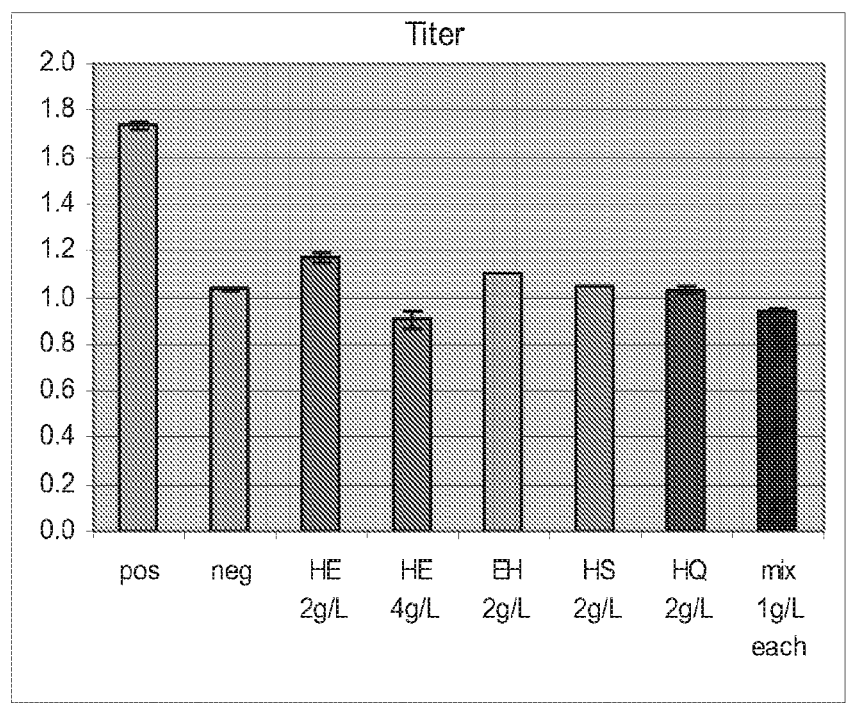
Figure 4B- Viability
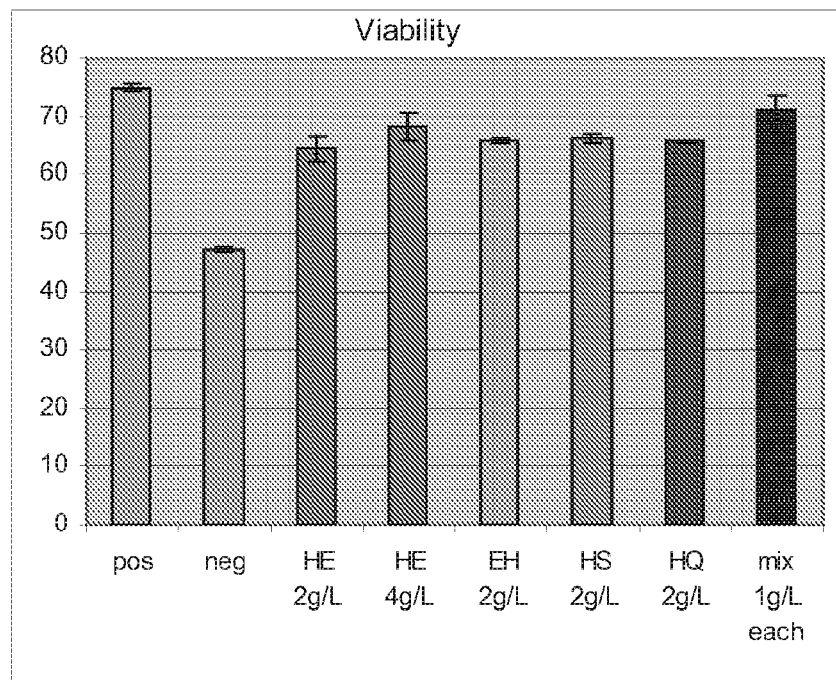

Figure 5- Effect of Various Di-peptides on Day 11 Titer from Cell Line C
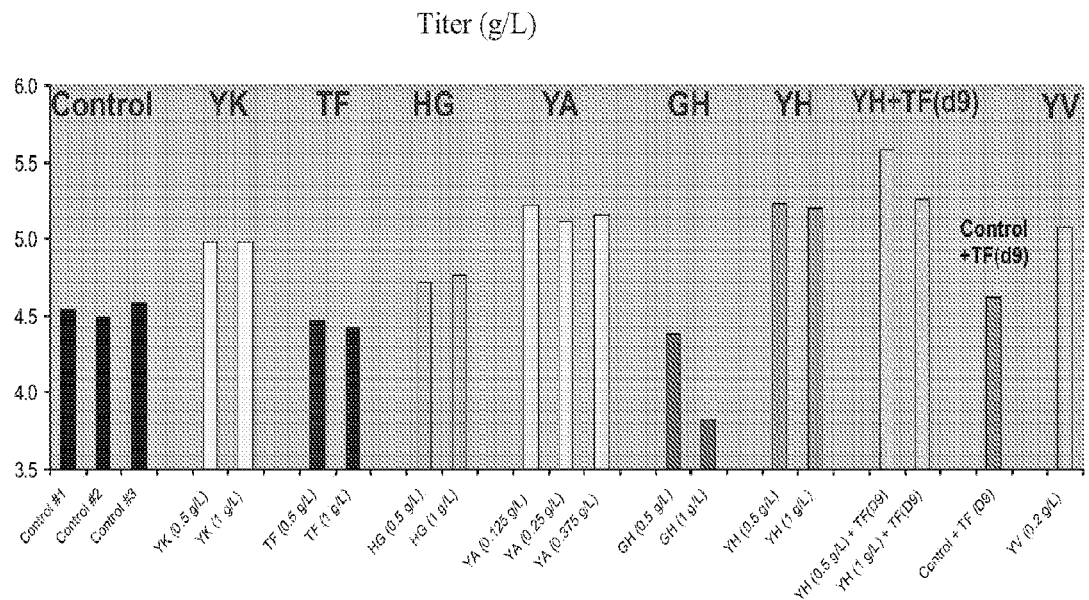
Figure 6- Increase in Cell Size in Cell Line C
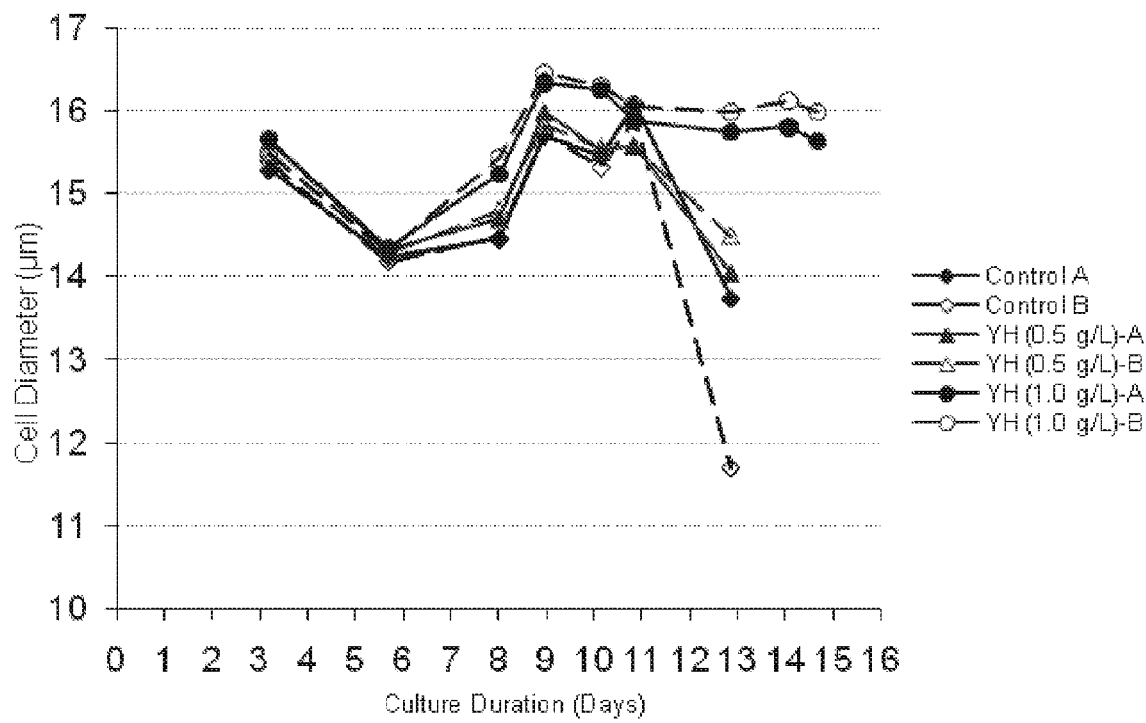

Figure 7- Improved titer (figure 7A) and culture viability (figure 7B) with Ala-His addition
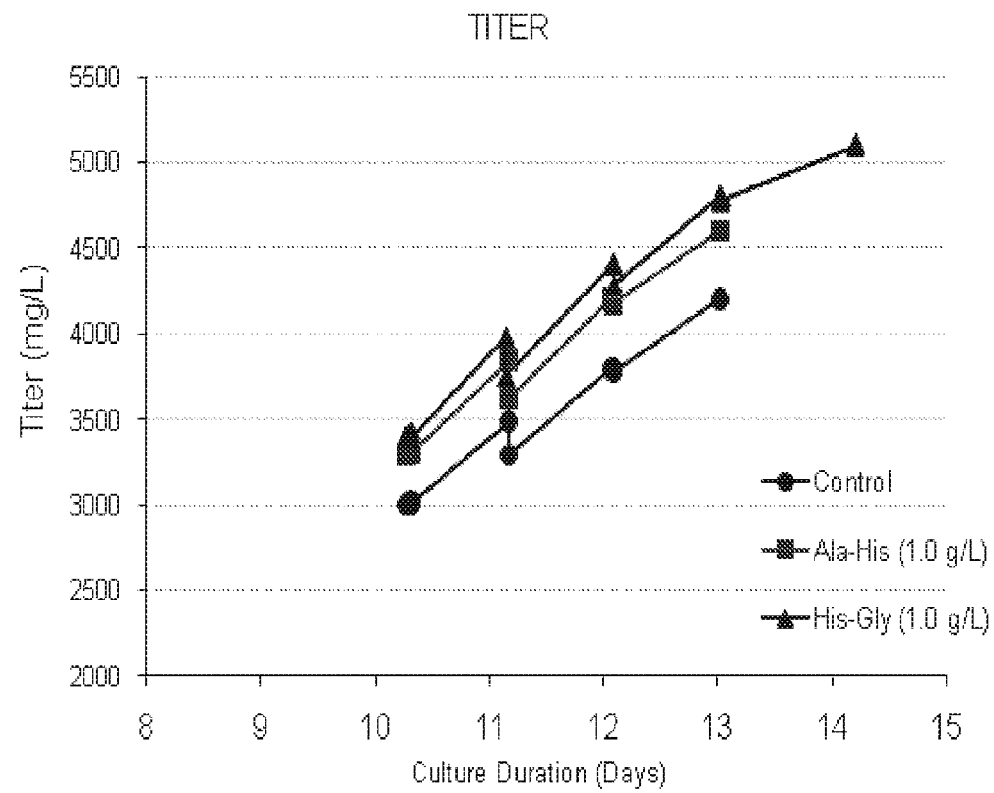
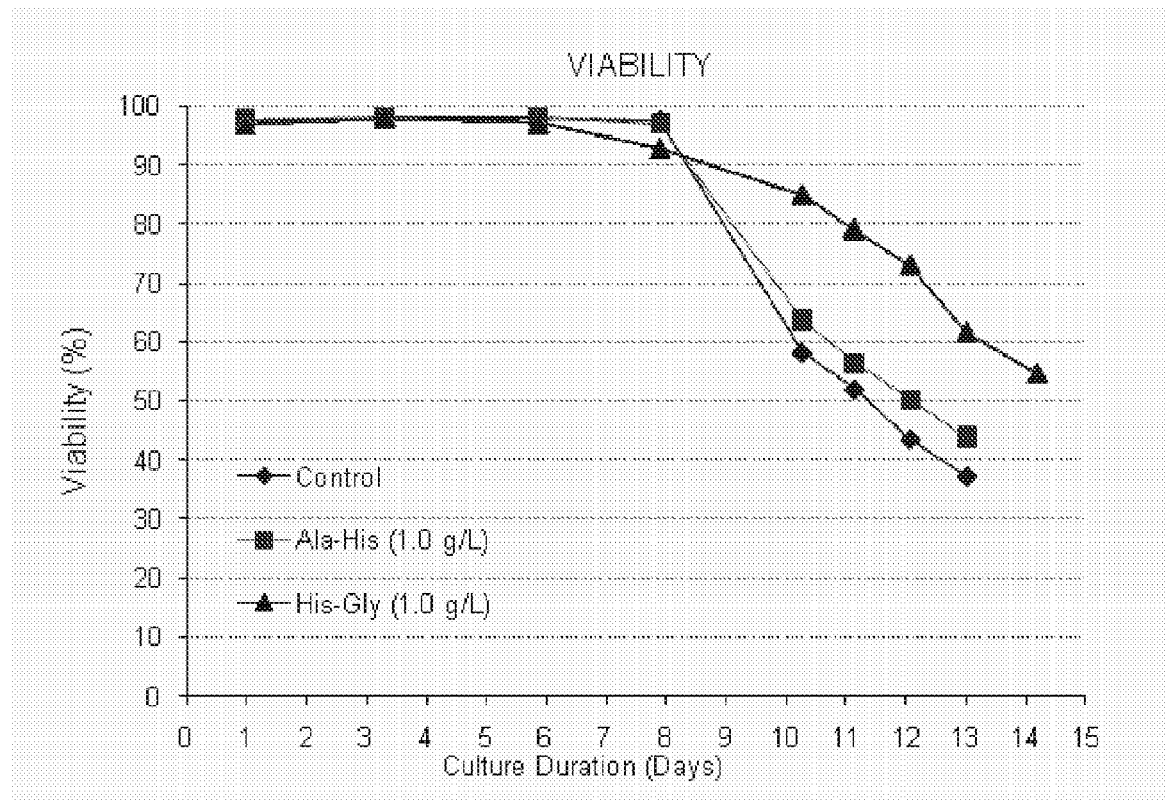

Figure 9A - Lactate profile in 2-L bioreactors with CHO cell line C: effect of Tyr-Lys (YK) and Tyr-His (YH) dipeptide addition.
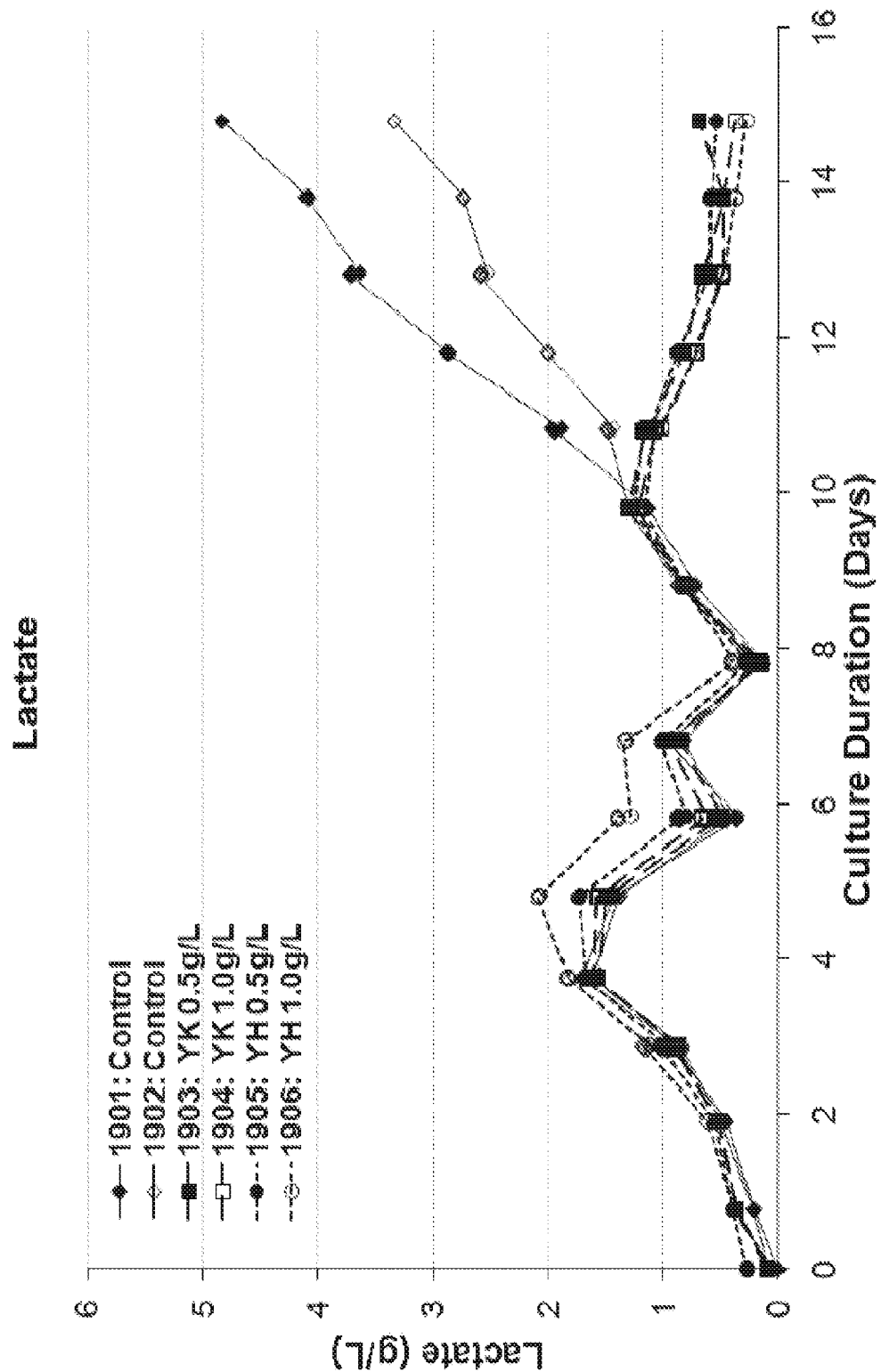

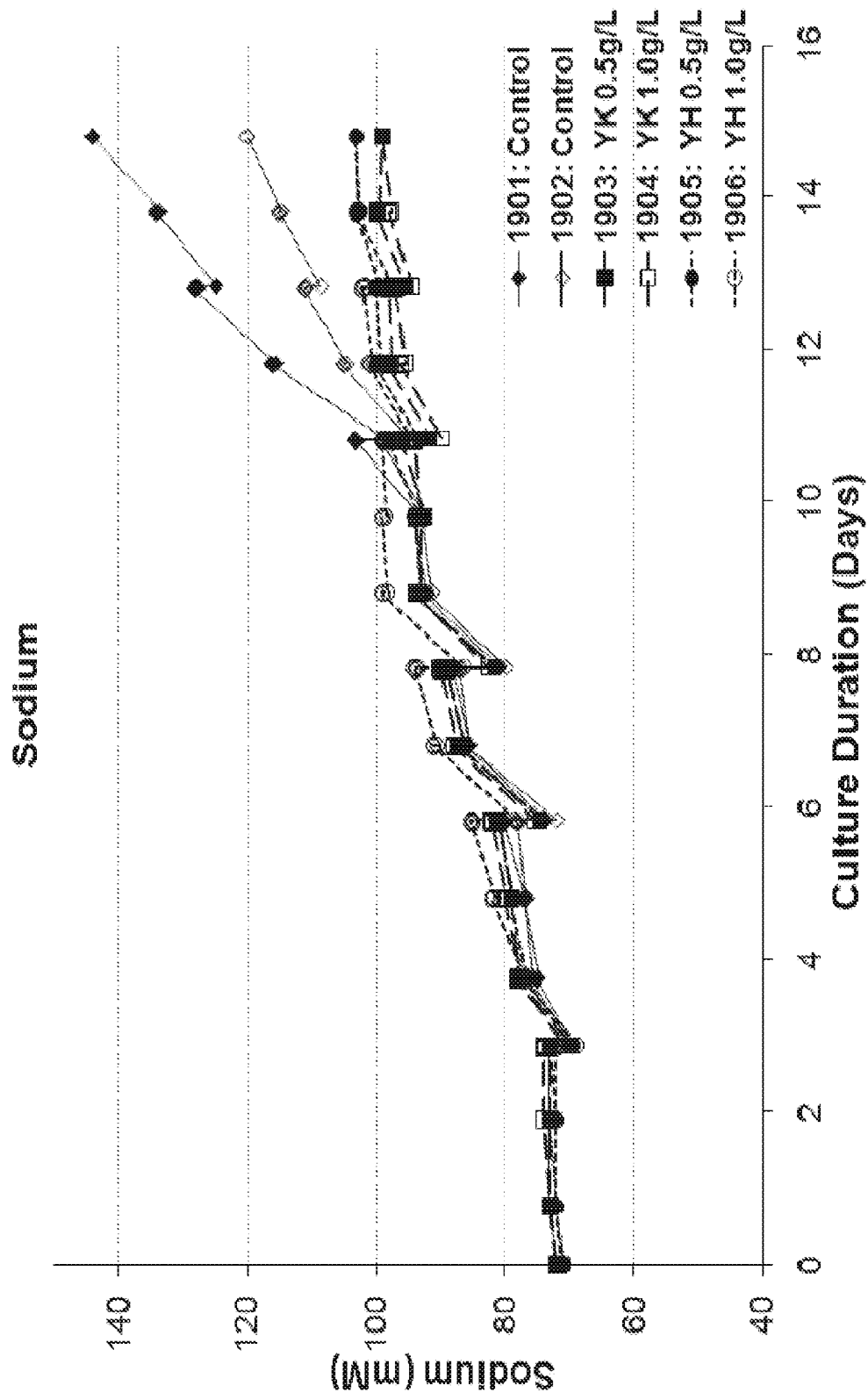
Figure 9B - Sodium (Na+) profile in 2-L bioreactors with CHO cell line C: Reduced levels of Na⁻ in Tyr-Lys (YK) and Tyr-His (YH) supplemented.

US 9,012,178 B2

DIPEPTIDES TO ENHANCE YIELD AND VIABILITY FROM CELL CULTURES

CROSS REFERENCE TO RELATED APPLICATIONS

This application is a National Stage application under 35 U.S.C. §371 of International Application No. PCT/US2011/046850 (designating the United States) having an international filing date of Aug. 5, 2011, which claims the benefit of U.S. Provisional Patent Application No. 61/371,119, filed Aug. 5, 2010, which is incorporated herein by reference in its entirety.

FIELD OF THE INVENTION

The invention is in the field of protein production in cultured recombinant cells.

BACKGROUND OF THE INVENTION

Therapeutic proteins and other commercially important polypeptides can be produced from mammalian cells in culture that have been engineered to express high levels of a particular protein or polypeptide of interest. One advantage of producing such proteins in mammalian cell cultures is that they can be designed for secretion, folding and post-translational modifications, such as glycosylation. In such mammalian cultures, control and optimization of cell culture conditions is critical for successful commercial production of proteins and polypeptides. The ultimate amount and quality of protein or polypeptide produced can be significantly affected by the cell culture conditions and reagents.

Supplementation of animal cell culture media with serum generally improves cell viability and also the production of recombinant proteins. Over the past decade or two, regulatory and safety concerns, as well as problems with sourcing heterogeneity, have driven an industry trend toward eliminating serum in commercial production of proteins. Grillberger et al., Biotechnol. J. 2009, 4, 186-201. However, animal cells grown in serum-free media can be very sensitive to nutritional deficiencies which may induce apoptosis. Apoptosis adversely affects both quality and titer of recombinant proteins. Franek and Fussenegger, 2005, Biotechnol. Prog. 21, 96-98. Protein hydrolysates or peptones generated from soy and wheat gluten can sometimes help compensate for the lack of serum. Much effort has been given to identifying the components in these additives, and their optimum concentration ranges, that are responsible for these advantageous effects.

Franek et al. prepared fractions from plant protein hydrolysates and tested them for their ability to support growth and secretion from murine hybridoma cells. Franek et al., 2000, Biotechnol. Prog. 16, 688-692. As an alternative approach, Franek et al. screened available synthetic peptides for their effect on production from a mouse monoclonal cell line in serum-free medium. Franek et al., 2002, Biotechnol. Prog. 18, 155-158. They reported that while single amino acid or dipeptide did not significantly alter the culture parameters, tri-, tetra-, and penta-glycine as well as tri- and tetra-alanine enhanced viable cell density and viability. Id. Certain tripeptides enhanced production of monoclonal antibody from this mouse monoclonal cell line. Id. In subsequent experiments on CHO cells recombinantly engineered to produce SEAP, this group reported that tetra-glycine increased viable cell density, and that the tri-peptide Gly-Lys-Gly enhanced SEAP production. Franek and Fussengger 2005, Biotechnol. Prog. 21, 96-98.

There remains a need in the art to develop methods for recombinant production of protein in completely defined—media or chemically defined media. While protein hydrolysates can improve survival, they remain a source of heterogeneity. Although certain tri- and tetra-peptides have been reported to improve culture parameters, it is preferable to have as simple and as defined a cell culture process as possible which maximizes recombinant protein titer. Any improvements to recombinant polypeptide expression, titer, cell growth and/or cell viability can lead to higher production levels, thereby reducing costs associated with the manufacture of protein therapeutics. The invention fulfills these needs by providing simple, easy and novel methods of increasing cell growth and protein production.

SUMMARY OF THE INVENTION

The invention provides a method of culturing animal cells that have been recombinantly engineered to express a protein of interest, the method comprising, growing the CHO cells in a serum-free medium during a growth phase, and growing the CHO cells in a serum-free defined production medium during a production phase, wherein during the production phase the serum-free medium is supplemented with at least one dipeptide selected from Tyr-His, Tyr-Lys, Tyr-Ala, Tyr-Val, His-Gly, and Ala-His, and wherein the titer of the protein is improved in the presence of the dipeptide or dipeptides as compared to the absence of the dipeptide or dipeptides. The invention also provides further supplementing the serum-free defined production medium with at least one dipeptide selected from Thr-Phe, His-Glu, Glu-His, His-Ser, and His-Gln. The addition of such dipeptides can further improve titer, and/or can improve the viability and viable cell density of the resulting production culture.

The invention further provides a method of culturing Chinese hamster ovary (CHO) cells that have been recombinantly engineered to express a protein, the method comprising growing the CHO cells in a serum-free medium during a growth phase, and growing the CHO cells in a serum-free defined production medium during a production phase, wherein during the production phase the serum-free medium is supplemented with at least one dipeptide selected from His-Glu, Glu-His, His-Ser, His-Gln, Tyr-His, Tyr-Lys, Tyr-Ala, Tyr-Val, His-Gly, and Ala-His, and wherein the viability of the cell culture is improved in the presence of the dipeptide or dipeptides as compared to the absence of the dipeptide or dipeptides.

Accordingly, using the methods of the invention, cell viability, viable cell density and expression of the protein of interest are improved relative to cells grown in chemically defined medium without dipeptides.

The present invention also provides an animal cell culture recombinantly engineered to express a protein, in a serum-free defined production medium supplemented with at least one dipeptide selected from Tyr-His, Tyr-Lys, Tyr-Ala, Tyr-Val, His-Gly, and Ala-His. The invention also provides an animal cell line in a serum-free defined production medium supplemented with at least one dipeptide selected from Thr-Phe, His-Glu, Glu-His, His-Ser and His-Gln.

Within the embodiments of the invention, the dipeptide can be added at a final concentration in the serum-free defined production medium from about 0.1 g/L to about 5 g/L. The dipeptide can also be added in a feed medium to the production phase. Also encompassed within the embodiments of the invention is the addition of two or more dipeptides. One embodiment is the addition of both dipeptides Tyr-His and Thr-Phe. The serum-free defined production medium can also contain putrescine and/or spermine and/or insulin-like growth factor type 1 (IGF-1).

Within the embodiments of the invention, the protein of interest can be a human antibody, a humanized antibody, a chimeric antibody, a recombinant protein, a recombinant fusion protein, growth factor, enzyme, or a cytokine.

BRIEF DESCRIPTION OF THE DRAWINGS

FIG. 1 shows the effect on titer (FIG. 1A) and culture viability (FIG. 1B) with the addition of various dipeptides as indicated to a production culture of cell line A.

FIG. 2 shows the effect on titer (FIG. 2A) and culture viability (FIG. 2B) with the addition of various dipeptides as indicated to a production culture of cell line B.

FIG. 3 shows the effect on titer (FIG. 3A) and culture viability (FIG. 3B) with the addition of various dipeptides as indicated to a production culture of cell line C.

FIG. 4 shows the effect on titer (FIG. 4A) and culture viability (FIG. 4B) with the addition of various His-containing dipeptides as indicated to a production culture of cell line D.

FIG. 5 shows the effect of various dipeptides as indicated on day 11 titer from cell line C.

FIG. 6 shows the increase in cell size over time in a production culture of cell line C.

FIG. 7 shows the improved titer (FIG. 7A) and culture viability (FIG. 7B) with Ala-His addition in cell line A.

FIG. 9 illustrates the resulting lactate profile (FIG. 9A) and sodium levels (FIG. 9B) of the same bioreactor experiment shown in FIG. 8.

DETAILED DESCRIPTION

Figure 8A:
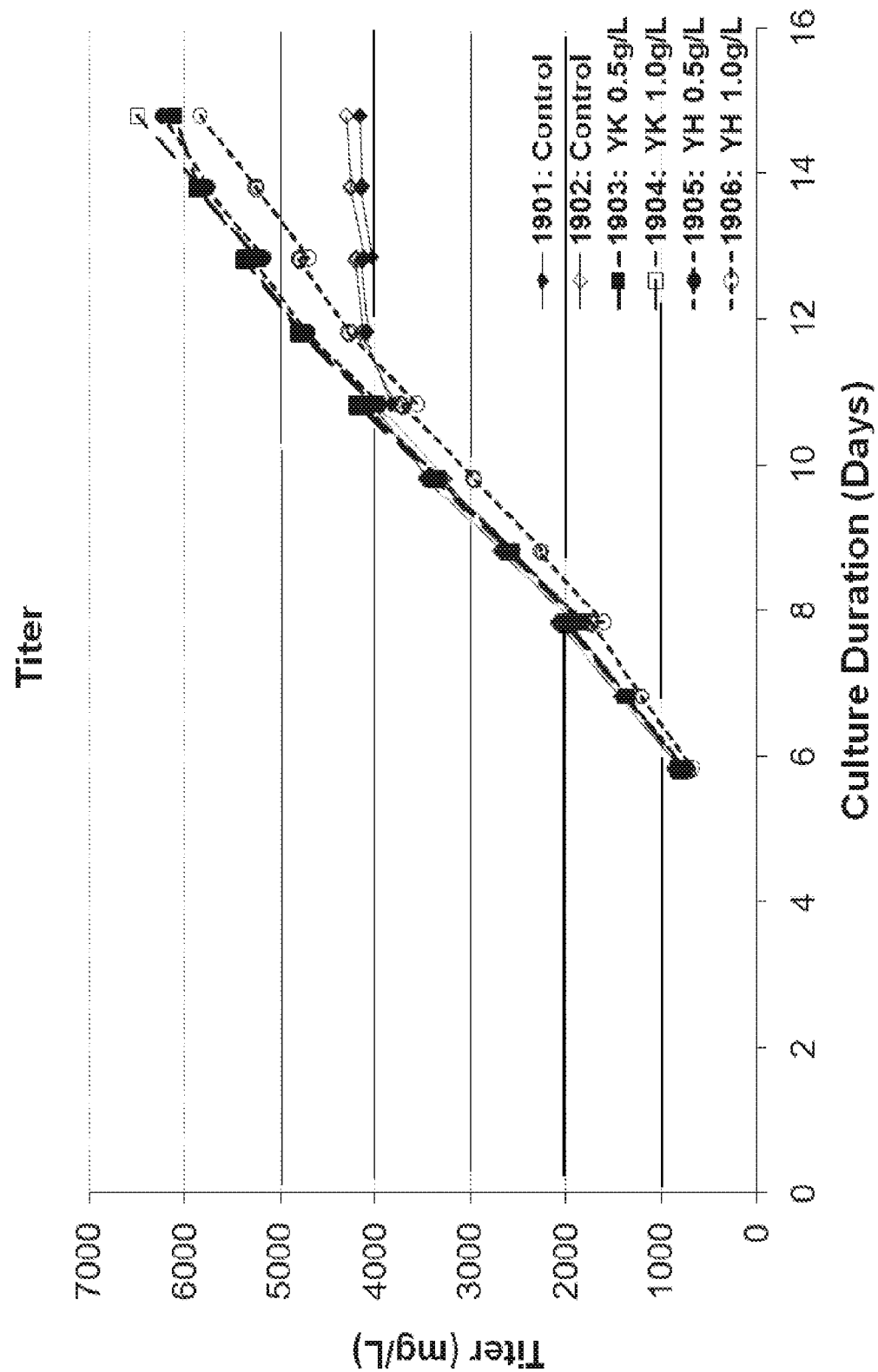
FIG. 8 is a bioreactor experiment that shows the improved titer (FIG. 8A) and culture viability (FIG. 8B) when either Tyr-Lys or Tyr-His are added at the indicated amounts to a production culture of cell line C.

The goal of these investigations is to develop serum-free, peptone-free media and/or cell culture formulations where each of the components is defined, and the media performs as well or exceeds that of serum- or peptone-supplemented media. Defined media formulations allow greater flexibility for optimization and improvements to cell growth and recombinant protein production including increasing cell growth rates, growth to high cell densities, controlling the stage and amount of cell differentiation, increasing protein secretion, increasing phenotypic and genetic stability and elimination of senescence for many cell types.

The invention includes a method of culturing Chinese hamster ovary (CHO) cells that have been recombinantly engineered to express a protein, the method comprising growing the CHO cells in a serum-free medium during a growth phase, and growing the CHO cells in a serum-free defined production medium during a production phase, wherein during the production phase the serum-free medium is supplemented with at least one dipeptide, and wherein the titer of the protein is improved in the presence of the dipeptide or dipeptides as compared to the absence of the dipeptide or dipeptides.

Various dipeptides have been tested for the ability to improve recombinant protein expression from CHO cells in chemically defined medium. The dipeptides that have been shown to improve titer include Tyr-His, Tyr-Lys, Tyr-Ala, Tyr-Val, His-Gly, and Ala-His. In addition, combinations of any of these dipeptides can also improve titer. As shown below by way of working examples, addition of these dipeptides is able to improve the titer of recombinant protein production as much as 10 to 20% or more (see Examples 2, 4, and 6). Such an improvement can result in significant cost savings in a commercial production process. These dipeptides also act to improve viability in the absence of peptones. While not wishing to be limited to any particular mechanism of action, it is thought that addition of these dipeptides seems to shift the metabolism of the cells from cell proliferation to cell productivity. This hypothesis is supported by the data provided below in Example 5.

In fact, dipeptide-supplemented cultures exhibited increased viability and specific productivity over control conditions beyond the conventional process duration of 11-days, allowing extention of the culture up to 15-days, as shown below in Example 7. In addition to showing enhanced viability and specific productivity, we also describe how dipeptide-supplemented cultures exhibited minimal nutrient depletion, improved metabolic profiles and pH maintenance. This effect is illustrated in Example 8. Accordingly, the methods of the invention also include a method of delaying or preventing lactate accumulation in CHO cells that have been recombinantly engineered to express a protein, the method comprising growing the CHO cells in a serum-free medium during a growth phase, and growing the CHO cells in a serum-free defined production medium during a production phase, wherein during the production phase the serum-free medium is supplemented with at least one dipeptide selected from Tyr-His and Tyr-Lys.

Additional dipeptides that can also be used in combination with the above recited dipeptides including Thr-Phe, as well as any number of other dipeptides. As shown below by way of working example, when used as a supplement by itself in serum-free, peptone-free production medium, Thr-Phe had little to no effect on viability and recombinant protein production. Tyr-His improved titer by approximately 15%. However, when Thr-Phe is added to a similar culture in combination with Tyr-His, titer was further improved, by as much as 20%.

Still other dipeptides can be added to the serum-free defined production medium, which peptides which have been shown to improve viable cell density and/or viability. These peptides are His-Glu, Glu-His, His-Ser, and His-Gln. As shown in Example 3 below, using these dipeptides in a cell culture can dramatically improve viability of a serum-free cell culture. Improving viability can improve product quality. Mixtures of such dipeptides can also be used in the cell culture to improve viability and/or VCD, as well as mixtures with the above dipeptides that are shown to increase titer. However, not all dipeptides were advantageous. For example, although His-Gly was able to improve productivity and culture performance of two different CHO cell lines expressing two different recombinant antibodies, Gly-His had a negative effect. This suggests that specific structural features of the dipeptide may be an important factor, and that certain dipeptides can actually confer negative impact.

Cells and Cell Culture: The invention finds particular utility in improving cell growth, viability and/or protein production via cell culture processes. The cell lines used in the invention are genetically engineered to express a polypeptide of commercial or scientific interest. Cell lines are typically derived from a lineage arising from a primary culture that can be maintained in culture for an unlimited time. Genetically engineering the cell line involves transfecting, transforming or transducing the cells with a recombinant polynucleotide molecule, and/or otherwise altering (e.g., by homologous recombination and gene activation or fusion of a recombinant cell with a non-recombinant cell) so as to cause the host cell to express a desired recombinant polypeptide. Methods and vectors for genetically engineering cells and/or cell lines to express a polypeptide of interest are well known to those of skill in the art; for example, various techniques are illustrated in *Current Protocols in Molecular Biology*, Ausubel et al., eds. (Wiley & Sons, New York, 1988, and quarterly updates); and Sambrook et al., Molecular Cloning: A Laboratory Manual (Cold Spring Laboratory Press, 1989); Kaufman, R. J., *Large Scale Mammalian Cell Culture*, 1990, pp. 15-69.

Animal cell lines are derived from cells whose progenitors were derived from a multi-cellular animal. One type of animal cell line is a mammalian cell line. A wide variety of mammalian cell lines suitable for growth in culture are available from the American Type Culture Collection (Manassas, Va.) and commercial vendors. Examples of cell lines commonly used in the industry include VERO, BHK, HeLa, CV1 (including Cos), MDCK, 293, 3T3, myeloma cell lines (e.g., NSO, NS1), SP2O, PC12, WI38 cells, Per.C6, and Chinese hamster ovary (CHO) cells.

The methods of the invention are exemplified using CHO cells. CHO cells are widely available and used in the industry for the production of commercial quantities of recombinant proteins. CHO cells are widely used for the production of complex recombinant proteins, e.g. cytokines, clotting factors, and antibodies (Brasel et al. (1996), *Blood* 88:2004-2012; Kaufman et al. (1988), *J. Biol Chem* 263:6352-6362; McKinnon et al. (1991), *J Mol Endocrinol* 6:231-239; Wood et al. (1990), *J. Immunol.* 145:3011-3016). Typically, the host CHO cells have a genetic background that is appropriate for transformation with a selectable marker. The most common CHO cell used as a host is the dihydrofolate reductase (DHFR) deficient cell line. The DHFR deficient mutant cell lines (Urlaub et al. (1980), *Proc Natl Acad Sci USA* 77: 4216-4220), DXB11 and DG-44, are desirable CHO host cell lines because the efficient DHFR selectable and amplifiable gene expression system allows high level recombinant protein expression in these cells (Kaufman R. J. (1990), *Meth Enzymol* 185:537-566). In addition, these cells are easy to manipulate as adherent or suspension cultures and exhibit relatively good genetic stability. Other selectable marker systems are also available for CHO cells. CHO cells and proteins recombinantly expressed in them have been extensively characterized and have been approved for use in clinical commercial manufacturing by regulatory agencies.

Recombinant Proteins: The methods of the invention can be used to culture cells that have been recombinantly engineered to express protein(s) of interest. The expressed protein (s) may be produced intracellularly or secreted into the culture medium from which it can be recovered and/or collected. In addition, the protein(s) can be purified, or partially purified, from such culture or component (e.g., from culture medium or cell extracts) using known processes and products available from commercial vendors. The purified protein(s) can then be "formulated", meaning buffer exchanged, sterilized, bulk-packaged, and/or packaged for a final user. Suitable formulations for pharmaceutical compositions include those described in *Remington's Pharmaceutical Sciences*, 18th ed. 1995, Mack Publishing Company, Easton, Pa.

Examples of polypeptides that can be produced with the methods of the invention include proteins comprising amino acid sequences identical to or substantially similar to all or part of one of the following proteins: tumor necrosis factor (TNF), flt3 ligand (WO 94/28391), erythropoeitin, thrombopoeitin, calcitonin, IL-2, angiopoietin-2 (Maisonpierre et al. (1997), *Science* 277(5322): 55-60), ligand for receptor activator of NF-kappa B (RANKL, WO 01/36637), tumor necrosis factor (TNF)-related apoptosis-inducing ligand (TRAIL, WO 97/01633), thymic stroma-derived lymphopoietin, granulocyte colony stimulating factor, granulocyte-macrophage colony stimulating factor (GM-CSF, Australian Patent No. 588819), mast cell growth factor, stem cell growth factor (U.S. Pat. No. 6,204,363), epidermal growth factor, keratinocyte growth factor, megakaryote growth and development factor, RANTES, human fibrinogen-like 2 protein (FGL2; NCBI accession no. NM_00682; Rüegg and Pytela (1995), *Gene* 160:257-62) growth hormone, insulin, insulinotropin, insulin-like growth factors, parathyroid hormone, interferons including α-interferons, γ-interferon, and consensus interferons (U.S. Pat. Nos. 4,695,623 and 4,897471), nerve growth factor, brain-derived neurotrophic factor, synaptotagmin-like proteins (SLP 1-5), neurotrophin-3, glucagon, interleukins, colony stimulating factors, lymphotoxin-β, leukemia inhibitory factor, and oncostatin-M. Descriptions of proteins that can be produced according to the inventive methods may be found in, for example, *Human Cytokines: Handbook for Basic and Clinical Research*, all volumes (Aggarwal and Gutterman, eds. Blackwell Sciences, Cambridge, Mass., 1998); *Growth Factors: A Practical Approach* (McKay and Leigh, eds., Oxford University Press Inc., New York, 1993); and *The Cytokine Handbook*, Vols. 1 and 2 (Thompson and Lotze eds., Academic Press, San Diego, Calif., 2003).

Additionally the methods of the invention would be useful to produce proteins comprising all or part of the amino acid sequence of a receptor for any of the above-mentioned proteins, an antagonist to such a receptor or any of the above-mentioned proteins, and/or proteins substantially similar to such receptors or antagonists. These receptors and antagonists include: both forms of tumor necrosis factor receptor (TNFR, referred to as p55 and p75, U.S. Pat. Nos. 5,395,760 and 5,610,279), Interleukin-1 (IL-1) receptors (types I and II; EP Patent No. 0460846, U.S. Pat. Nos. 4,968,607, and 5,767, 064), IL-1 receptor antagonists (U.S. Pat. No. 6,337,072), IL-1 antagonists or inhibitors (U.S. Pat. Nos. 5,981,713, 6,096,728, and 5,075,222) IL-2 receptors, IL-4 receptors (EP Patent No. 0 367 566 and U.S. Pat. No. 5,856,296), IL-15 receptors, IL-17 receptors, IL-18 receptors, Fc receptors, granulocyte-macrophage colony stimulating factor receptor, granulocyte colony stimulating factor receptor, receptors for oncostatin-M and leukemia inhibitory factor, receptor activator of NF-kappa B (RANK, WO 01/36637 and U.S. Pat. No. 6,271,349), osteoprotegerin (U.S. Pat. No. 6,015,938), receptors for TRAIL (including TRAIL receptors 1, 2, 3, and 4), and receptors that comprise death domains, such as Fas or Apoptosis-Inducing Receptor (AIR).

Other proteins that can be produced using the invention include proteins comprising all or part of the amino acid sequences of differentiation antigens (referred to as CD proteins) or their ligands or proteins substantially similar to either of these. Such antigens are disclosed in *Leukocyte Typing VI* (*Proceedings of the VIth International Workshop and Conference*, Kishimoto, Kikutani et al., eds., Kobe, Japan, 1996). Similar CD proteins are disclosed in subsequent workshops. Examples of such antigens include CD22, CD27, CD30, CD39, CD40, and ligands thereto (CD27 ligand, CD30 ligand, etc.). Several of the CD antigens are members of the TNF receptor family, which also includes 41BB and OX40. The ligands are often members of the TNF family, as are 41BB ligand and OX40 ligand.

Enzymatically active proteins or their ligands can also be produced using the invention. Examples include proteins comprising all or part of one of the following proteins or their ligands or a protein substantially similar to one of these: a disintegrin and metalloproteinase domain family members including TNF-alpha Converting Enzyme, various kinases, glucocerebrosidase, superoxide dismutase, tissue plasminogen activator, Factor VIII, Factor IX, apolipoprotein E, apolipoprotein A-I, globins, an IL-2 antagonist, alpha-1 antitrypsin, ligands for any of the above-mentioned enzymes, and numerous other enzymes and their ligands.

The invention can also be used to produce antibodies or portions thereof. The term "antibody" includes reference to both glycosylated and non-glycosylated immunoglobulins of any isotype or subclass or to an antigen-binding region thereof that competes with the intact antibody for specific binding, unless otherwise specified, including human, humanized, chimeric, multi-specific, monoclonal, polyclonal, and oligomers or antigen binding fragments thereof. Antibodies can be any class of immunoglobulin. Also included are proteins having an antigen binding fragment or region such as Fab, Fab', F(ab')$_2$, Fv, diabodies, Fd, dAb, maxibodies, single chain antibody molecules, complementarity determining region (CDR) fragments, scFv, diabodies, triabodies, tetrabodies and polypeptides that contain at least a portion of an immunoglobulin that is sufficient to confer specific antigen binding to a target polypeptide. The term "antibody" is inclusive of, but not limited to, those that are prepared, expressed, created or isolated by recombinant means, such as antibodies isolated from a host cell transfected to express the antibody.

Examples of antibodies include, but are not limited to, those that recognize any one or a combination of proteins including, but not limited to, the above-mentioned proteins and/or the following antigens: CD2, CD3, CD4, CD8, CD11a, CD14, CD18, CD20, CD22, CD23, CD25, CD33, CD40, CD44, CD52, CD80 (B7.1), CD86 (B7.2), CD147, IL-1α, IL-1β, IL-2, IL-3, IL-7, IL-4, IL-5, IL-8, IL-10, IL-2 receptor, IL-4 receptor, IL-6 receptor, IL-13 receptor, IL-18 receptor subunits, FGL2, PDGF-β and analogs thereof (see U.S. Pat. Nos. 5,272,064 and 5,149,792), VEGF, TGF, TGF-β2, TGF-β1, EGF receptor (see U.S. Pat. No. 6,235,883) VEGF receptor, hepatocyte growth factor, osteoprotegerin ligand, interferon gamma, B lymphocyte stimulator (BlyS, also known as BAFF, THANK, TALL-1, and zTNF4; see Do and Chen-Kiang (2002), *Cytokine Growth Factor Rev.* 13(1): 19-25), C5 complement, IgE, tumor antigen CA125, tumor antigen MUC1, PEM antigen, LCG (which is a gene product that is expressed in association with lung cancer), HER-2, a tumor-associated glycoprotein TAG-72, the SK-1 antigen, tumor-associated epitopes that are present in elevated levels in the sera of patients with colon and/or pancreatic cancer, cancer-associated epitopes or proteins expressed on breast, colon, squamous cell, prostate, pancreatic, lung, and/or kidney cancer cells and/or on melanoma, glioma, or neuroblastoma cells, the necrotic core of a tumor, integrin alpha 4 beta 7, the integrin VLA-4, B2 integrins, TRAIL receptors 1, 2, 3, and 4, RANK, RANK ligand, TNF-α, the adhesion molecule VAP-1, epithelial cell adhesion molecule (EpCAM), intercellular adhesion molecule-3 (ICAM-3), leukointegrin adhesin, the platelet glycoprotein gp IIb/IIIa, cardiac myosin heavy chain, parathyroid hormone, rNAPc2 (which is an inhibitor of factor VIIa-tissue factor), MHC I, carcinoembryonic antigen (CEA), alpha-fetoprotein (AFP), tumor necrosis factor (TNF), CTLA-4 (which is a cytotoxic T lymphocyte-associated antigen), Fc-γ-1 receptor, HLA-DR 10 beta, HLA-DR antigen, L-selectin, Respiratory Syncitial Virus, human immunodeficiency virus (HIV), hepatitis B virus (HBV), *Streptococcus mutans*, and *Staphlycoccus aureus*. Specific examples of known antibodies which can be produced using the methods of the invention include but are not limited to adalimumab, bevacizumab, infliximab, abciximab, alemtuzumab, bapineuzumab, basiliximab, belimumab, briakinumab, canakinumab, certolizumab pegol, cetuximab, conatumumab, denosumab, eculizumab, gemtuzumab ozogamicin, golimumab, ibritumomab tiuxetan, labetuzumab, mapatumumab, matuzumab, mepolizumab, motavizumab, muromonab-CD3, natalizumab, nimotuzumab, ofatumumab, omalizumab, oregovomab, palivizumab, panitumumab, pemtumomab, pertuzumab, ranibizumab, rituximab, rovelizumab, tocilizumab, tositumomab, trastuzumab, ustekinumab, zalutumumab, and zanolimumab.

The invention can also be used to produce recombinant fusion proteins comprising, for example, any of the above-mentioned proteins. For example, recombinant fusion proteins comprising one of the above-mentioned proteins plus a multimerization domain, such as a leucine zipper, a coiled coil, an Fc portion of an immunoglobulin, or a substantially similar protein, can be produced using the methods of the invention. See e.g. WO94/10308; Lovejoy et al. (1993), *Science* 259:1288-1293; Harbury et al. (1993), *Science* 262: 1401-05; Harbury et al. (1994), *Nature* 371:80-83; Håkansson et al. (1999), *Structure* 7:255-64. Specifically included among such recombinant fusion proteins are proteins in which a portion of a receptor is fused to an Fc portion of an antibody such as etanercept (a p75 TNFR:Fc), and belatacept (CTLA4:Fc).

Media and Culture: The methods of the invention entail growing animal cells in cell culture medium. For the purposes of this invention, cell culture medium is a media suitable for growth of animal cells, such as mammalian cells, in in vitro cell culture. Cell culture media formulations are well known in the art. Typically, cell culture media are comprised of buffers, salts, carbohydrates, amino acids, vitamins and trace essential elements. The cell culture medium may or may not contain peptone, and/or proteins. Various tissue culture media, including serum-free and defined culture media, are commercially available, for example, any one or a combination of the following cell culture media can be used: RPMI-1640 Medium, RPMI-1641 Medium, Dulbecco's Modified Eagle's Medium (DMEM), Minimum Essential Medium Eagle, F-12K Medium, Ham's F12 Medium, Iscove's Modified Dulbecco's Medium, McCoy's 5A Medium, Leibovitz's L-15 Medium, and serum-free media such as EX-CELL™ 300 Series (JRH Biosciences, Lenexa, Kans.), among others. Other examples of serum-free defined cell media can be found in U.S. Pat. No. 7,294,481 and WO 2006/026445, both of which are incorporated by reference herein. Cell culture media may be supplemented with additional or increased concentrations of components such as amino acids, salts, sugars, vitamins, hormones, growth factors, buffers, antibiotics, lipids, trace elements and the like, depending on the requirements of the cells to be cultured and/or the desired cell culture parameters. For example, cell culture media may be supplemented with polyamines such as putrescine, spermidine and spermine, to improve cell growth, cell viability, and/or recombinant protein production in association with a particular cell. The serum-free cell culture medium can comprise spermine or spermidine at a concentration of at least about 0.1 µM, or putrescine at a concentration of at least about 100 µM, or carnosine. (See, for example, WO 2008/154014 and WO 2007/050498, both of which are incorporated by reference herein.)

Cell culture media may be serum-free, protein-free, and/or peptone-free media. "Serum-free" medium applies to a cell culture medium that does not contain animal sera, such as fetal bovine serum. "Protein-free" applies to cell culture media free from exogenously added protein, such as transferrin, protein growth factors IGF-1, or insulin. Protein-free media may or may not contain peptones. "Peptone-free"

applies to cell culture media which contains no exogenous protein hydrolysates such as animal and/or plant protein hydrolysates. Eliminating serum and/or hydrolysates from cell culture media has the advantage of reducing lot to lot variability and enhancing processing steps, such as filtration. However, when serum and/or peptone are removed from the cell culture media, cell growth, viability and/or protein expression may be diminished or less than optimal. As such, serum-free and/or peptone-free cell culture medium may be highly enriched for amino acids, trace elements and the like. See, for example, U.S. Pat. Nos. 5,122,469 and 5,633,162. Although there are many media formulations, there is a need to develop defined media formulations that perform as well or preferably better than those containing animal sera and/or peptones.

Serum-free defined production medium refers to an enriched medium that is formulated without serum, peptones, or other animal and/or plant hydrolysates. Such defined cell culture formulations can contain amino acids, inorganic salts, carbohydrates, lipids, vitamins, buffers and trace essential elements. Optionally, such defined cell culture formulations can contain exogenously added protein, as long as the source of the protein is defined and pure, and preferably recombinantly produced.

By cell culture or "culture" is meant the growth and propagation of cells outside of a multicellular organism or tissue. Suitable culture conditions for mammalian cells are known in the art. See e.g. Animal cell culture: A Practical Approach, D. Rickwood, ed., Oxford University Press, New York (1992). Mammalian cells may be cultured in suspension or while attached to a solid substrate. Fluidized bed bioreactors, hollow fiber bioreactors, roller bottles, shake flasks, or stirred tank bioreactors, with or without microcarriers, and operated in a batch, fed batch, continuous, semi-continuous, or perfusion mode are available for mammalian cell culture. Cell culture media and/or concentrated feed media may be added to the culture continuously or at intervals during the culture. For example, a culture may be fed once per day, every other day, every three days, or may be fed when the concentration of a specific medium component, which is being monitored, falls outside a desired range.

Animal cells, such as CHO cells, may be cultured in small scale cultures, such as for example, in 100 ml containers having about 30 ml of media, 250 ml containers having about 80 to about 90 ml of media, 250 ml containers having about 150 to about 200 ml of media. Alternatively, the cultures can be large scale such as for example 1000 ml containers having about 300 to about 1000 ml of media, 3000 ml containers having about 500 ml to about 3000 ml of media, 8000 ml containers having about 2000 ml to about 8000 ml of media, and 15000 ml containers having about 4000 ml to about 15000 ml of media.

Large scale cell cultures, such as for clinical manufacturing of protein therapeutics, are typically maintained for days, or even weeks, while the cells produce the desired protein(s). During this time the culture can be supplemented with a concentrated feed medium containing components, such as nutrients and amino acids, which are consumed during the course of the culture. Concentrated feed medium may be based on just about any cell culture media formulation. Such a concentrated feed medium can contain most of the components of the cell culture medium at, for example, about 5×, 6×, 7×, 8×, 9×, 10×, 12×, 14×, 16×, 20×, 30×, 50×, 100×, 200×, 400×, 600×, 800×, or even about 1000× of their normal amount. Concentrated feed media are often used in fed batch culture processes.

The methods according to the present invention may be used to improve the production of recombinant proteins in both single phase and multiple phase culture processes. In a single phase process, cells are inoculated into a culture environment and the disclosed methods are employed during the single production phase. In a multiple stage process, cells are cultured in two or more distinct phases. For example, cells may be cultured first in one or more growth phases, under environmental conditions that maximize cell proliferation and viability, then transferred to a production phase, under conditions that maximize protein production. In a commercial process for production of a protein by mammalian cells, there are commonly multiple, for example, at least about 2, 3, 4, 5, 6, 7, 8, 9, or 10 growth phases that occur in different culture vessels preceding a final production phase. The growth and production phases may be preceded by, or separated by, one or more transition phases. In multiple phase processes, the methods according to the present invention can be employed at least during the production phase, although they may also be employed in a preceding growth phase. A production phase can be conducted at large scale. A large scale process can be conducted in a volume of at least about 100, 500, 1000, 2000, 3000, 5000, 7000, 8000, 10,000, 15,000, 20,000 liters. A growth phase may occur at a higher temperature than a production phase. For example, a growth phase may occur at a first temperature from about 35° C. to about 38° C., and a production phase may occur at a second temperature from about 29° C. to about 37° C., optionally from about 30° C. to about 36° C. or from about 30° C. to about 34° C. In addition, chemical inducers of protein production, such as, for example, caffeine, butyrate, and hexamethylene bisacetamide (HMBA), may be added at the same time as, before, and/or after a temperature shift. If inducers are added after a temperature shift, they can be added from one hour to five days after the temperature shift, optionally from one to two days after the temperature shift.

Accordingly, the methods of the invention entail growing the CHO cells in a serum-free medium during a growth phase such that the cells increase in number to a desired concentration. The serum-free medium during the growth phase may or may not contain protein hydrolysates. The growth phase may entail multiple batch and/or fed batch phases, or may entail a perfusion phase. After the desired quantity and/or viable cell density of cells is achieved, the cells are then grown in a production phase. The cells in serum-free medium from the growth phase are typically seeded into a serum-free defined production medium for the production phase. As noted above, the serum-free defined production medium is formulated without peptones or other animal and/or protein hydrolysates. However, since the cells from the growth phase have been diluted into serum-free defined production medium, there can be carry-over of some hydrolysates and/or peptones from the growth phase if such components were used during previous phases. Typical seeding densities into the production phase can be from $2\times10^5$ cells/mL to $5\times10^6$ cells/mL.

During at least the production phase, the serum-free medium is supplemented with at least one dipeptide selected from Tyr-His, Tyr-Lys, Tyr-Ala, Tyr-Val, His-Gly, Ala-His. When one or more of these dipeptides is added to the culture, the titer of recombinant protein is improved in the presence of the dipeptide or dipeptides as compared to the absence of the dipeptide or dipeptides. In addition, when the dipeptide Thr-Phe is also added along with one of the above listed dipeptides, titer is further increased.

Other dipeptides can also be added. Some particular dipeptides which have been shown to improve viable cell density (VCD) and/or viability are His-Glu, Glu-His, His-Ser, and His-Gln. VCD refers to the total number of cells that are surviving in the cell culture medium in a particular volume, generally per ml. Viability refers to the number of cells which are alive compared to the total number of cells, both dead and alive, expressed as a percentage. Mixtures of such dipeptides can also be used in the cell culture to improve viability and/or VCD, as well as mixtures with the above dipeptides that are shown to increase titer. Increasing viability and/or VCD is highly desirable because it avoids apoptosis and results in higher product quality. Accordingly, these dipeptides can also be used alone or in combination, even without the addition of the dipeptides which have been shown to increase titer (specifically, Tyr-His, Tyr-Lys, Tyr-Ala, Tyr-Val, His-Gly, Ala-His, and His-Glu).

The dipeptide can be included in the serum-free defined production medium, and/or it can be added as part of a concentrated feed medium. Such feed medium can be added to the culture after one or more days, and can also be added repeatedly during the course of the production phase. For example, the production phase can last from 7 days to as long as 8, 9, 10, 11, 12, 13, or 14 days or longer. The culture can be supplemented with the dipeptide(s) immediately and/or on days 2, 3, 4, 5, 6, 7, 8, 9, 10, 11, 12, and/or 13. Typically, the final concentration of the dipeptide in the culture is about from 0.01 to 10 g/L, more typically about 0.05 to 6 g/L, and even more typically about 0.1 to 4 g/L, and still more typically about 0.2 to 2 g/L. Of course, if multiple dipeptides are used in a single cell culture, the total dipeptide concentration can be higher. In one embodiment, the range of dipeptide(s) is from about 0.1 to about 5 g/L.

The protein expressed by the methods of the invention can be collected. In addition the protein can be purified, or partially purified, from such culture or component (e.g., from culture medium or cell extracts or bodily fluid) using known processes. The phrase "partially purified" means that some fractionation procedure, or procedures, have been carried out, but that more polypeptide species (at least 10%) than the desired protein is present. By "purified" is meant that the protein is essentially homogeneous, i.e., less than 1% contaminating proteins are present. Fractionation procedures can include but are not limited to one or more steps of filtration, centrifugation, precipitation, phase separation, affinity purification, gel filtration, ion exchange chromatography, size exclusion chromatography (SEC), hydrophobic interaction chromatography (HIC; using such resins as phenyl ether, butyl ether, or propyl ether), HPLC, or some combination of above.

The invention also optionally encompasses further formulating the protein. By the term "formulating" is meant that the protein can be buffer exchanged, sterilized, bulk-packaged and/or packaged for a final user. For purposes of the invention, the term "sterile bulk form" means that a formulation is free, or essentially free, of microbial contamination (to such an extent as is acceptable for food and/or drug purposes), and is of defined composition and concentration.

The term "sterile unit dose form" means a form that is appropriate for the customer and/or patient administration or consumption. Such compositions can comprise an effective amount of the protein, in combination with other components such as a physiologically acceptable diluent, carrier, or excipient. The term "physiologically acceptable" means a non-toxic material that does not interfere with the effectiveness of the biological activity of the active ingredient(s).

The invention having been described, the following examples serve to illustrate details of the invention, but are not intended to limit its scope in anyway.

EXAMPLE 1

Preliminary results using a chemically defined medium indicated that tyrosine appeared to be depleted during the production process for a recombinant antibody. However, tyrosine is a poorly soluble amino acid, so it was difficult to increase the concentration of tyrosine in the medium. Therefore, it was theorized that dipeptides containing tyrosine could be used to replenish tyrosine. Several different dipeptides were tested for solubility as indicated in the following Table 1.

TABLE 1

| Dipeptide | pI (#1) | pI (#2) | Solubility (g/L)- ref. #1 | Solubility (g/L)- ref. #2 | Tyr content (g/L) | Solubility tested |
| --- | --- | --- | --- | --- | --- | --- |
| Tyr-His | 6.45 | 7.53 | 100 | | 56 | readily soluble |
| Tyr-Lys | 8.16 | 9.49 | 81 | | 43 | readily soluble |
| Ala-Tyr | 4.84 | 5.86 | 56 | 14 | 40 | Difficult to dissolve (takes long time) |
| Met-Tyr | 4.58 | 5.67 | information not available | | | Not soluble (white, milky ppt) |

Since Tyr-His and Tyr-Lys were readily soluble under these testing conditions, cell culture experiments were designed to test them as an additive in serum free, peptone-free medium.

EXAMPLE 2

Introduction: In this experiment, Tyr-His and Tyr-Lys were tested as an additive to an enriched defined medium containing IGF-1 and putrescine.

Materials and Methods: Dipeptides were purchased from Bachem (Torrance, Calif.). Each dipeptide was dissolved in water for preparation of concentrated stock solution (100 mg/mL), followed by sterile filtration using Spin-X® filter unit (Corning Inc., Corning, N.Y.).

On Day 0, prior to inoculation of production cell lines, appropriate volumes of concentrated dipeptide stock solution were added to serum-free defined production medium to bring the final dipeptide concentration at 0.5-2.0 g/L. For controls, the same volume of water was added. Cells were inoculated at $5 \times 10^5$ cells/mL with the final culture volume of 50 mL in 250 mL flasks. The shaker flasks cultures were grown in the incubator at 36° C., with 5% CO2 and agitation rate of 160 rpm.

Cultures were fed with bolus defined feed media on Days 3, 6, and 8 with the feed volume of 5-6% on Day 3, 9% on Day 6 and 9% on Day 8. Cultures were stopped and harvested on Day 11. However, if the culture viability on Day 11 was >70%, culture duration was extended beyond day 11 by introducing $4^{th}$ feed on Day 11 and $5^{th}$ feed on day 13 if necessary. Feed volume on Day 11 ranged from 5% to 8%, depending on the culture performance. Day 13 feed ranged from 2.5% to 3.0%. Glucose was fed as needed with typical target concentration of 7-8 g/L.

On selective days during the production run, small volumes of cultures were taken out to assess viable cell density and % viability using the CEDEX cell counter (Roche Innovatis AG). Titer was also determined on collected samples, using the high-throughput HPLC analytical method.

Results: In this series of experiments, the effect of two dipeptides, Tyr-His and Tyr-Lys, was tested on three different CHO cell lines. Each cell line was recombinantly engineered to express a different human antibody.

FIG. 1 illustrates the results obtained with cell line A tested with Tyr-His (labeled as YH) and Tyr-Lys (labeled as YK) at 2 g/L, 1 g/L, and 0.5 g/L final concentration in the serum-free defined production medium. Significant improvements in both titer and viability at day 13 and day 14 were observed for both of the peptides at all three concentrations tested. Day 14 titer and viability were not determined for "Control" since D13 viability was below 50%.

FIG. 2 illustrates the results obtained for cell line B. YH is addition of Tyr-His at 1 g/L, YK is addition of Tyr-Lys at 1 g/L, and YH+YK is the combination of both Tyr-His and Tyr-Lys, with each individual dipeptide at a concentration of 0.5 g/L. Again, titer and viability are significantly increased.

FIG. 3 illustrates the results obtained for cell line C. Tyr-His was tested at 0.5 g/L and 1 g/L. Tyr-Lys was tested at 0.5 g/L and 1 g/L. Again, titer and viability are significantly increased.

Tyr-His and Tyr-Lys were subsequently tested on two additional CHO cell lines, and they also improved both titer and viability in a similar manner in one cell line, and to a lesser extent in a fifth cell line (data not shown).

EXAMPLE 3

In a series of in-house peptone fractionation experiments, an attempt was made to characterize or isolate the components in peptones which conferred advantageous properties in cell culture. It was speculated that casein-derived peptides containing the amino acid His may be of interest, and a several different synthetic peptides containing His were chosen for further investigation.

Materials and Methods: CHO cell line D, which produces a fully human recombinant antibody, was used for this experiment. Cells were inoculated at $2 \times 10^6$ cells/mL with a final culture volume of 2.0 mL into serum-free defined production medium. Experimental samples contained the dipeptides His-Glu, Glu-His, His-Ser, and His-Gln from 1 to 4 g/L. Control wells were set up containing either no added dipeptide as a negative control, or containing peptone at 10 g/L as a positive control. The cultures were incubated as a batch culture for 6 days, at which point the cells were harvested and titer and viability determined.

Results: The dipeptides His-Glu, Glu-His, His-Ser, and His-Gln were tested for their ability to substitute for peptone in a serum-free defined medium. The effect of each of these peptides is shown in FIG. 4. Although titer was not significantly increased over the negative control (FIG. 4A), viability was significantly improved in the presence of each of these dipeptides, as well as a combination of the four dipeptides (FIG. 4B). However, the combination of the four dipeptides exhibited only slightly better viability than each on their own.

EXAMPLE 4

In this example, the effect of a variety of tyrosine- and histidine-containing dipeptides was tested on cell line C. In addition, since Phe is the precursor to Tyr, a dipeptide of Thr-Phe was also tested.

Materials and Methods: CHO cell line C was cultured as in Example 2. The dipeptides tested were Tyr-Lys, Thr-Phe, His-Gly, Tyr-Ala, Gly-His, Tyr-His, Tyr-Val, and a combination of Tyr-His and Thr-Phe. The culture period was 11 days, at which point titer and viability were assessed.

Results: The results are shown in FIG. 5. Tyr-Lys, Tyr-Ala, Tyr-His, and Tyr-Val all significantly improved titer. His-Gly moderately improved titer, Thr-Phe had little to no effect, and Gly-His adversely affected titer in this experiment and with this cell line.

EXAMPLE 5

In this experiment, an attempt was made to try and determine the mechanism behind the Tyr-His induced titer and viability improvements. Therefore, additional parameters of the cell culture grown in the presence of Tyr-His were examined.

Materials and Methods: CHO cell line C was used for this experiment, and cultured as in Example 2. Titer, viability, viable cell density, specific productivity, and cell diameter were determined each day from day 6 to 13 or 14 of cell culture. Tyr-His dipeptide was tested at 0.5 g/L and 1 g/L, and compared to the addition of no dipeptide.

Results: As before, Tyr-His significantly improved both culture viability and recombinant protein titer in this CHO cell line. In addition, growth (measured as both Viable Cell Density and Integrated Cell Density) was suppressed when Tyr-His was added to the culture. The suppression was greater at the higher concentration of 1 g/L than it was at 0.5 g/L. In addition, the specific productivity of the cells was maintained in the cultures containing Tyr-His from days 10 to 14 in a concentration responsive manner. In contrast, the control cells without dipeptide exhibited a severe drop-off in productivity during the latter stages of the cell culture. It was hypothesized that the addition of Tyr-His induced a metabolic switch from cellular proliferation to productivity. This was supported by the data showing slower growth, increased specific productivity (Qp) and increased cell size with dipeptide addition. The increase in cell size results are shown in FIG. 6. In addition, the cultures containing Tyr-His dipeptide additions exhibited better pH control, lactate profile, and ammonium profile than the control cultures.

EXAMPLE 6

In this example, the effect of an Ala-His dipeptide was tested on recombinant protein titer and viability of CHO cell line A.

Materials and Methods: CHO cell line A was cultured as in Example 2. The effect of dipeptide Ala-His (added at 1 g/L) was compared to no added dipeptide (control) and dipeptide His-Gly. The culture period was 13 to 14 days, at which point titer and viability were assessed.

Results: The results are shown in FIG. 7. His-Gly improved titer by more than 10% as compared to control. Ala-His also improved titer, but not as much as His-Gly. His-Gly was also better at maintaining viability, especially in the later stages of this cell culture. However, Ala-His did exhibit the ability to maintain increased viability, especially the earlier stages of culture with this cell line.

EXAMPLE 7

Viability and Titer in Bioreactors

The beneficial effects of synthetic dipeptides Tyr-His and Tyr-Lys that were observed in shake flasks were reproduced in bioreactors using CHO cell line C.

Materials and Methods: A bioreactor experiment examining the performance of CHO cell line C with tyrosine-histidine (YH) and tyrosine-lysine (YK) dipeptides was performed. Six 2-L bioreactors were run under the following conditions: a control condition was performed in duplicate, while the remaining reactors were fed 0.5 g/L YH, 1.0 g/L YH, 0.5 g/L YK, and 1.0 g/L YK (singlet for each condition). The starting volume was 1500±50 ml with an inoculation density of $5\times10^5$ cells/ml and a temperature set point of 36.0° C., pH setpoint of 6.95, DO setpoint of 48 mm Hg, agitation rate at 315 rpm, and two-sided pH control. The process was extended to 15 days with a feed schedule of Day 3 (5%), Day 6 (9%), Day 8 (9%) plus additional feeds on Day 11 (5%) and Day 13 (2.5%). Daily glucose feeds (up to 7 g/L on Days 3-11; up to 5 g/L Days 12-14) and antifoam (as needed; up to 25 ppm) were also introduced.

Small volumes of cultures were taken daily to assess viable cell density and cell viability using the Cedex AS20 cell counter (Roche Innovatis, Beilefed, Germany). Metabolic data were obtained from the Nova Bioprofile 100 Plus (Nova Biomedical, Waltham, Mass.), and an Advanced Instrument (Norwood, Mass.) osmometer model 2020 was used to measure osmolality. A Chiron Model 248 blood gas analyzer (Siemens Healthcare Diagnostics, Deerfield, Ill.) was used to measure pH, dissolved carbon dioxide, and dissolved oxygen.

Titer and amino acid content were also determined using conditioned media taken during the production duration. Centrifuged supernatant was frozen at −20° C. and stored for later titer and amino acid analyses. Titer values were measured using affinity Protein A followed by HPLC analysis. Appropriate extinction coefficient values were applied for each molecule to determine the final titer. The amino acid analysis method utilized the AccuTag reagent kit and the pre-column derivatization chemistry. Derivatization, chromatography, and data analysis steps were performed according to the instructions provided by the vendor recommendations (Waters Corporation, Milford, Mass.).

Figure 8B:
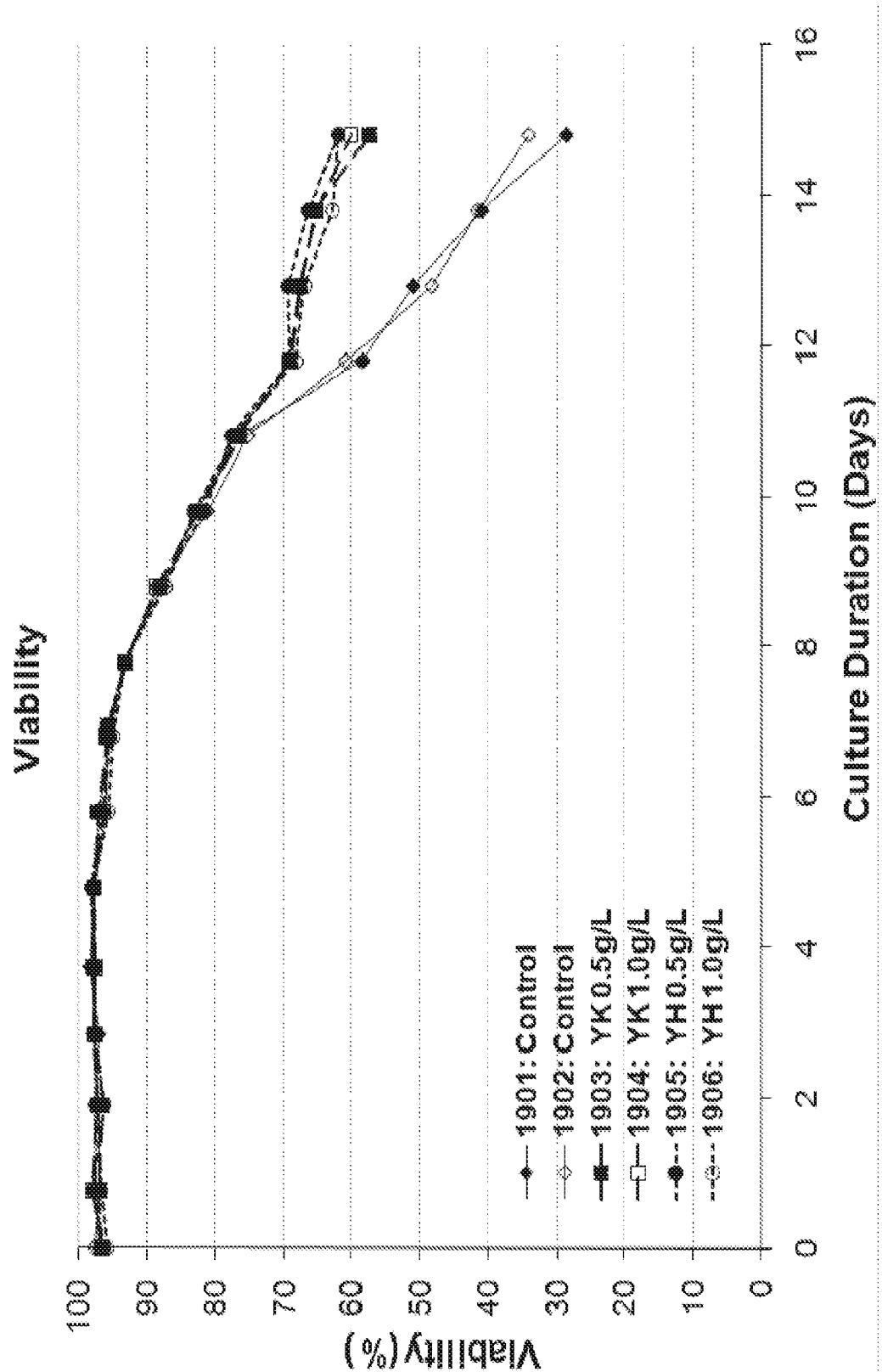

Results: In 2 liter vessels, both Tyr-His and Tyr-Lys dipeptides significantly enhanced titer (see FIG. 8A) and specific productivity in the pH-controlled bioreactor environment. In addition, both dipeptides were able to extend culture duration by improving culture viability (see FIG. 8B). Volumetric productivity continued to increase beyond day 11 for dipeptide supplemented cultures.

EXAMPLE 8

Improved Metabolic Profiles in Dipeptide Supplemented Cultures

Materials and Methods: In the bioreactor experiments run in Example 6, lactate and ammonium (NH4+) profiles were monitored. In addition, free Tyrosine, Histidine, Lysine, and asparagines levels were monitored from day 6 to day 15 of the culture.

Results: In correlation with titer and viability improvement, enhanced metabolic profiles were achieved with dipeptide addition. In the bioreactor experiment, the control reactors began accumulating lactate on Day 10 (FIG. 9A), while dipeptide-supplemented bioreactors consumed lactate during the same timeframe. Concomitant with lactate accumulation, the $Na^+$ levels also started to rise in the control reactors (FIG. 9B), reflecting exogenously added buffer, sodium bicarbonate, in response to the drop in pH. However, the $Na^+$ level was well maintained in dipeptide supplemented conditions, most likely due to their ability to maintain relatively constant pH. These data suggest that supplemental dipeptides can prevent media acidification occurring in the latter phase of production runs, thereby requiring less base addition.

Similar to bioreactor results for this cell line, improved lactate profiles were observed in shaker conditions (data not shown). However, lactate consumption was observed only with a higher concentration (1.0 g/L YH) of dipeptide. When a lower amount (0.5 g/L YH) was added, lactate accumulation could not be prevented, but was delayed. These results correlate with the pH profile of the culture. At the higher dipeptide concentration (1.0 g/L), pH was maintained at a relatively constant level while at the lower dipeptide concentration (0.5 g/L), a significant decrease in pH was detected. However, the extent of this pH drop was less severe in the lower dipeptide concentration condition than in the "control" condition. Since shaker conditions do not have externally fed bicarbonate buffer for pH control, higher levels of dipeptide may be required to achieve a similar level of benefit as in the bioreactors.

Improved $NH_4^+$ profiles were also observed in dipeptide-supplemented conditions (data not shown). However, similar to the lactate profiles, shaker conditions were more sensitive to dipeptide concentrations than bioreactors, in terms of reducing $NH_4^+$ levels.

Amino acid analyses from the bioreactor experiment indicated that in control reactors, both tyrosine (Tyr) and asparagine (Asn) are depleted by Day 11. In contrast, tyrosine depletion was not detected in Tyr-Lys or Tyr-His supplemented conditions. However, neither of these synthetic dipeptides could rescue the cultures from asparagine depletion. In contrast to the tyrosine profile, which differed significantly between the control and dipeptide conditions, the asparagine profile remained relatively comparable among different conditions. Eventual depletion of tyrosine on Day 15 was observed with lower dipeptide levels (0.5 g/L of either YH or YK), while cultures with higher dipeptide concentrations (1.0 g/L of either YH or YK) never experienced tyrosine depletion during the 15-day culture period. These results suggest that free tyrosine is being liberated from dipeptides during the course of production. With higher dipeptide supplementation (1.0 g/L), a higher amount of free tyrosine became available. Since neither Tyr-Lys nor Tyr-His contains the Asn moiety, asparagine levels were not affected. Interestingly, higher levels of free tyrosine were observed in 1.0 g/L YH condition than the 1.0 g/L YK condition. This may be partially due to repressed cell growth observed in the 1.0 g/L YH condition (data not shown).

Higher histidine (His) levels were observed in His-containing dipeptide conditions only (i.e. Tyr-His), further supporting the idea that these dipeptides are being dissociated over time into free amino acids. A very distinct difference in the histidine levels was observed between lower (0.5 g/L) versus higher (1.0 g/L) YH conditions, even as early as Day 6. Since amino acid analysis data was only obtained from day 6 onward, it is not possible at this point to determine exactly when these dipeptides started to decompose into free amino acids.

Lysine profiles also displayed a dose-dependent increase in free lysine levels in YK-supplemented conditions (FIG. 7D). However, the difference in lysine levels was less obvious in the 0.5 g/L YK-fed condition as compared to conditions receiving no YK supplement. For example, the free lysine levels detected in YH-supplemented conditions (either at YH 0.5 g/L or YH 1.0 g/L) is similar to the lysine level detected in the 0.5 g/L of YK-supplemented condition on Day 9 and also on Day 15 (FIG. 7D). This could be due to inefficient consumption of lysine by YH-treated cultures.

Bioreactor results suggest that tyrosine depletion in CHO cell line C cells has a deleterious effect on specific productivity (Qp). Tyrosine depletion observed on Day 11 in the control reactors correlates with a sharp decrease in Qp. In contrast, an increase in Qp is observed in dipeptide-supplemented conditions with higher levels of tyrosine available.

This functional correlation between tyrosine and Qp is again observed between Days 14 and 15, during which a sharp decline in Qp is observed in cultures supplemented with lower dipeptide concentrations (i.e. in YK 0.5 g/L and YH 0.5 g/L supplemented conditions) Amino acid profiles indicate that during this timeframe, tyrosine is completely depleted in 0.5 g/L dipeptide conditions. In contrast, sufficient levels of tyrosine were available in 1.0 g/L dipeptide conditions on Day 15, and high Qp was maintained).

The present invention is not to be limited in scope by the specific embodiments described herein that are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. A method of culturing Chinese hamster ovary (CHO) cells that have been recombinantly engineered to express a protein, the method comprising growing the CHO cells in a serum-free medium during a growth phase, and growing the CHO cells in a serum-free defined production medium during a production phase, wherein during the production phase the serum-free medium is supplemented with at least one dipeptide selected from Tyr-His, Tyr-Lys, His-Gly, and Ala-His, and wherein the titer of the protein is improved in the presence of the dipeptide or dipeptides as compared to the absence of the dipeptide or dipeptides.

2. The method of claim 1, wherein the dipeptide is added at a final concentration in the serum-free defined production medium from about 0.1 g/L to about 5 g/L.

3. The method of claim 1, wherein the dipeptide is added in a feed medium to the production phase.

4. The method of claim 1, wherein at least two dipeptides are added.

5. The method of claim 4, wherein one dipeptide is Thr-Phe, His-Glu, Glu-His, His-Ser or His-Gln.

6. The method of claim 5, wherein the dipeptides comprise Tyr-His and Thr-Phe.

7. The method of claim 1, wherein the serum-free defined production medium contains putrescine and/or spermine.

8. The method of claim 1, wherein the serum-free defined production medium contains insulin-like growth factor type 1 (IGF-1).

9. The method of claim 1, wherein the protein is a human antibody, a humanized antibody, a chimeric antibody, a recombinant fusion protein, or a cytokine 10. A cell culture comprising a Chinese hamster ovary (CHO) cell line recombinantly engineered to express a protein, a serum-free defined production medium supplemented with at least one dipeptide selected from Tyr-His, Tyr-Lys, His-Gly, and Ala-His.

11. The cell culture of claim 10, wherein the dipeptide concentration is about 0.1 g/L to about 5 g/L.

12. The cell culture of claim 10, wherein the serum-free defined production medium is formulated without peptone.

13. The cell culture of claim 10 comprising at least two dipeptides.

14. The cell culture of claim 13, wherein one dipeptide is Thr-Phe, His-Glu, Glu-His, His-Ser or His-Gln.

15. The cell culture of claim 14, wherein the dipeptides comprise Tyr-His and Thr-Phe.

16. The cell culture of claim 10, wherein the serum-free defined production medium contains putrescine, spermine, and/or insulin-like growth factor type 1 (IGF-1).

17. The cell culture of claim 10, wherein the protein is a human antibody, a humanized antibody, a chimeric antibody, a recombinant fusion protein, or a cytokine.

18. A method of culturing Chinese hamster ovary (CHO) cells that have been recombinantly engineered to express a protein, the method comprising growing the CHO cells in a serum-free medium during a growth phase, and growing the CHO cells in a serum-free defined production medium during a production phase, wherein during the production phase the serum-free medium is supplemented with at least one dipeptide selected from His-Glu, His-Ser, His-Gln, Tyr-His, Tyr-Lys, His-Gly, and Ala-His, and wherein the viability of the cell culture is improved in the presence of the dipeptide or dipeptides as compared to the absence of the dipeptide or dipeptides.

19. The method of claim 18, wherein the dipeptide is added at a final concentration in the serum-free defined production medium from about 0.2 g/L to about 5 g/L.

20. The method of claim 18, wherein the dipeptide is added in a feed medium to the production phase.

21. The method of claim 18, wherein at least two dipeptides are added.

22. The method of claim 18, wherein the serum-free defined production medium contains putrescine and/or spermine.

23. The method of claim 18, wherein the serum-free defined production medium contains insulin-like growth factor type 1 (IGF-1).

24. The method of claim 18, wherein the protein is a human antibody, a humanized antibody, a chimeric antibody, a recombinant fusion protein, or a cytokine

* * * * *